United States Patent [19]

Quinlan

[11] 4,206,233
[45] Jun. 3, 1980

[54] MICROBIOCIDAL QUATERNARIES OF HALOGEN DERIVATIVES OF ALKYNOXYMETHYL AMINES

[75] Inventor: Patrick M. Quinlan, Webster Groves, Mo.

[73] Assignee: Petrolite Corporation, St. Louis, Mo.

[21] Appl. No.: 957,629

[22] Filed: Nov. 3, 1978

Related U.S. Application Data

[60] Division of Ser. No. 556,331, Mar. 7, 1975, abandoned, which is a continuation of Ser. No. 957,615, Nov. 3, 1978.

[51] Int. Cl.$^2$ .................................................. A01N 9/20
[52] U.S. Cl. .................................... 424/329; 424/285; 260/567.6 M; 260/567.6 P; 260/567.6 H; 252/390; 252/148
[58] Field of Search ................................ 424/329, 285

[56] References Cited

U.S. PATENT DOCUMENTS

| | | | |
|---|---|---|---|
| 3,201,467 | 8/1965 | Oakes | 260/567.6 M |
| 3,792,084 | 2/1974 | Quinlan | 424/199 |
| 4,111,679 | 9/1978 | Shair et al. | 424/329 |

*Primary Examiner*—V. D. Turner
*Attorney, Agent, or Firm*—Sidney B. Ring; Hyman F. Glass

[57] ABSTRACT

This invention relates to quaternaries of halogen derivatives of alkynoxymethyl amines and uses thereof. These may be summarized by the following formulae:

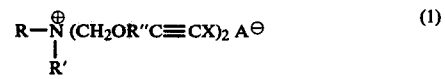

where R and R' are substituted groups such as alkyl, aryl, etc.; R" is an alkylidene group; and X is halogen and A is an anion; and

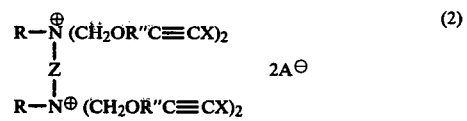

where R, R' and R" having the same meaning as in (1) and Z is a bridging group, preferably hydrocarbon such as alkylene, alkinylene, alkenylene, arylene, etc.

7 Claims, No Drawings

MICROBIOCIDAL QUATERNARIES OF HALOGEN DERIVATIVES OF ALKYNOXYMETHYL AMINES

This is a division of application Ser. No. 556,331, filed Mar. 7, 1975. Ser. No. 556,331 is now abandoned. Copending Ser. No. 957,615, filed on Nov. 3, 1978, is a continuation of Ser. No. 556,331.

Application Ser. No. 556,331 filed Mar. 7, 1975 relates to halogen derivatives of alkynoxymethyl amines, and most preferably halogen derivatives of bis (alkynoxymethyl) amines, and to uses for these compositions particularly as corrosion inhibitors. The present invention relates to quaternaries of the halogen derivatives of alkynoxymethyl amines of Ser No. 556,332.

The halogen derivatives of Ser. No. 556,332 derived from the compositions of Ser. No. 496,145 filed Aug. 9, 1974 are ideally illustrated by the following equation:

$$RNH_2 + CH_2O + R'OH \rightarrow RN(CH_2OR')_2$$

where R is a substituted group, preferably hydrocarbon such as alkyl, aryl, aralkyl cycloalkyl, etc., and substituted derivatives thereof, etc., and R' is an alkynyl moiety.

The reaction of Ser. No. 496,145 is carried out by reacting the amine, aldehyde, and acetylenic alcohol under dehydrating conditions. The alkynoxymethyl amine is formed. In practice the amine is gradually added to a mixture of formaldehyde and acetylenic alcohol in an azeotropic solvent at reflux until the theoretical amount of water is removed. Thereupon the product is separated from the reaction mixture, for example by distillation under reduced pressure.

A wide variety of amines having at least one primary group can be employed. They include aliphatic, cycloaliphatic, aryl, heterocyclic, etc. amines. These amines may or may not contain other groups. The following are representative examples.

n-Butyl amine
2-ethylhexyl amine
Monoisopropanolamine
Hexylamine
Heptylamine
Octylamine
Decylamine
Furfurylamine
Dodecylamine
Monoethanolamine
n-Amylamine
Sec-amylamine
2-amino-4-methylpentane
4-amino-2-butanol
5-isopropylamino-1-pentanol Also, high molecular weight aliphatic amines known as Armeen 10, Armeen 16D, Armeen HTD, Armeen 18D, and Armeen CD can be used. ($RNH_2$). Armeens are a series of amines possessing aliphatic chains ranging from 8 to 18 carbons. Armeen 18D has the composition 97% primary amine of which 93% is octadecyl amine, according to Zimmerman and Lavine, Handbook, of Material Trade Names, 1953, page 62.

Amines having ring structures include cyclohexylamine, and various comparable amines with alkyl substitutents in the ring.

Similarly, an amine, presumably obtained from Rosin Amine D and acrylonitrile, can be prepared. The structure of Rosin Amine D is as follows:

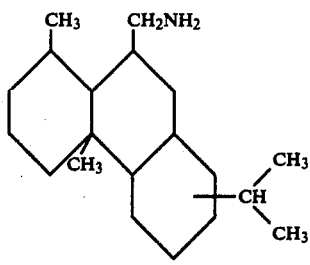

The acetylenic alcohols employed in the present invention may suitably include ethyl octynol, propargyl alcohol, hexynol and other acetylenic alcohols having the structural formula:

$$H-C\equiv C-R''-OH$$

where R'' is

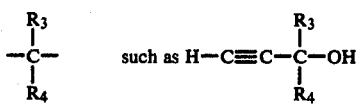

where $R_3$ is selected from the group consisting of $CH_3$ and H and $R_4$ is selected from the group consisting of hydrogen, alkyl groups having 1 to 18 carbon atoms, naphthalyl, phenyl, and alkyl substituted phenyls having 1 to 10 carbon atoms in the alkyl substituent. Examples of such alcohols include: methyl butynol, methyl pentynol, hexynol, ethyl octynol, propargyl alcohol, benzyl butynol, naphthalyl butynol, and the like.. Acetylenic alcohols which contain 3 to 10 carbon atoms are preferred.

Althouh formaldehyde is preferred, other aldehydes or ketones may be employed in place of formaldehyde such as those of the formula $$R_1-C=O$$
$$\phantom{R_1-C=}|$$
$$\phantom{R_1-C=}R_2$$

where $R_1$ and $R_2$ are hydrogen or a hydrocarbon group such as alkyl, i.e., methyl, ethyl, propyl, butyl, etc.; aryl, i.e., phenol, alkyl phenyl, etc., benzyl; cycloalkyl, i.e., cyclohexyl, etc. Thus, the $-CH_2-$ group in the formula $$RN(CH_2OR')_2$$

also may include substituted $-CH_2-$ groups $$RN(\underset{R_2}{\overset{R_1}{\underset{|}{\overset{|}{C}}}}-OR')_2$$

where the $R_1$ and $R_2$ are hydrogen or group derived from the aldehyde or ketone.

The preparation of halogen derivatives of alkynoxymethyl alkyl amines is illustrated in Ser. No. 556,332 filed Mar. 7, 1975 and may be ideally illustrated by the following equation:

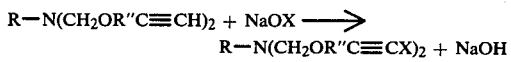

where R is a substituted group, preferably hydrocarbon such as alkyl, aryl, cycloalkyl, etc. and substituted derivatives thereof, etc., R″ is an alkylidene moiety, and X is halogen. Specific R groups illustrated herein include alkyl groups in the range of 3 to 18 carbon atoms, benzyl and cyclohexyl.

The preparation of the halogen derivatives may be accomplished by the reaction of an alkali halide such as potassium iodide, sodium bromide and the like with sodium hypo-chlorite in the presence of the N,N-Di(Alkynoxymethyl) alkyl amine. Thus the appropriate hypohalite is generated in situ in the presence of the acetylenic moiety to produce the desired halogen derivative. In brief a typical reaction would be:

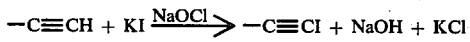

Typically the acetylenic moiety is mixed with an aqueous solution of the alkali halide. To this mixture is added, with cooling, the sodium hypochlorite. The mixture is then stirred at room temperature for prolonged periods of time. In most cases the acetylenic moiety is insoluble in the reaction medium. Thus the yields are decreased, and the length of the reaction is increased. The method may be improved considerably by adding an emulsifying agent, phenolethoxylates, sodium stearate, and the like. to the reaction mixture. This allows an intimate mixture of the acetylenic moiety and the alkali hypohalite to be obtained by agitation. The products are isolated by extraction and identified by analytical methods.

(1) EXAMPLES OF MONOFUNCTIONAL QUATERNIZING AGENTS

Any hydrocarbon halide, e.g., alkyl, alkenyl, cycloalkenyl, aralkyl, etc., halide which contains at least one carbon atom and up to about thirty carbon atoms or more per molecule can be employed to alkylate the products of this invention. It is especially preferred to use alkyl halides having between about one to about eighteen carbon atoms per molecule. The halogen portion of the alkyl halide reactant molecule can be any halogen atom, i.e., chlorine, bromine, fluorine, and iodine. In practice, the alkyl bromides and chlorides are used, due to their greater commercial availability. Non-limiting examples of the alkyl halide reactant are methyl chloride; ethyl chloride; propyl chloride; n-butyl chloride; sec-butyl iodide; t-butyl fluoride; n-amyl bromide; isoamyl chloride, n-hexyl bromide; n-hexyl iodide; heptyl fluoride; 2-ethyl-hexyl chloride; n-octyl bromide; decyl iodide; dodecyl bromide; 7-ethyl-2-methyl-undecyl iodide; tetradecyl bromide; hexadecyl bromide; hexadecyl fluoride; heptadecyl chloride; octadecyl bromide; docosyl chloride, tetracosyl iodide; hexacosyl bromide; octacosyl chloride; and triacontyl chloride. In addition, alkenyl halides can also be employed, for example, the alkenyl halides corresponding to the above examples. In addition, the halide may contain other elements besides carbon and hydrogen, as, for example, where dichloroethylether is employed.

The alkyl halides can be chemically pure compounds or of commercial purity. Mixtures of alkyl halides, having carbon chain lengths falling within the range specified hereinbefore, can also be used. Examples of such mixtures are mono-chlorinated wax and mono-chlorinated kerosene. Complete instructions for the preparation of mono-chlorowax have been set forth in U.S. Pat. No. 2,238,790.

Thus, the term quaternizing as employed herein and in the claims include alkenylation, cycloalkenylation, aralkylation, etc., and other hydrocarbonylation as well as alkylation itself.

(2) EXAMPLES OF DIFUNCTIONAL QUATERNIZING AGENTS

X—Z—X may be a wide variety of compounds, capable of joining amino groups, where Z may be alkylene, alkenylene, alkynylene, alkaralkylene, an alkylene-ether-containing group, an ester-containing group, etc., and X is a halide.

The following are non-limiting examples:

(I) Saturated dihalides

X—Z—X where Z is alkylene, straight chain or branched, for example X(CH$_2$)$_n$X where n is 2–25 or more, for example 2–10, but preferably 2–4. The

may be branched such as where at least one of the H's is a hydrocarbon group such as alkyl, i.e., methyl, ethyl, etc., substituted such as halo, hydroxy, etc.

(II) Aralkylene dihalides

X—Z—X where Z is aralkylene having for example 8–30 or more carbons, such as 8–20 carbons, but preferably xylylene.

The following are illustrative examples:

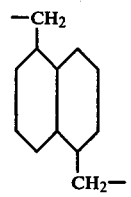

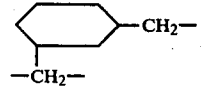

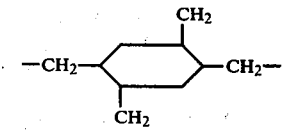

-continued

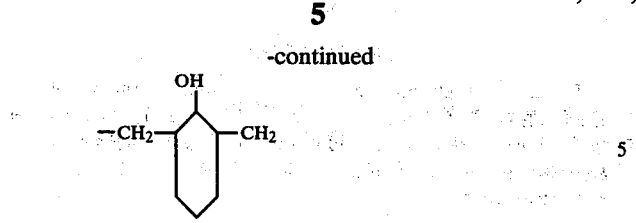

Additional examples of aralkylene radicals include those of the formula —CH$_2$—Ar—CH$_2$— where Ar is

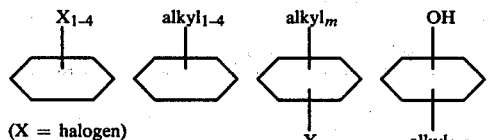

(X = halogen)

(where n + m = 1-4)

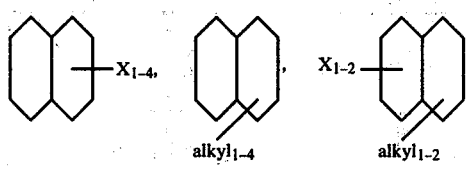

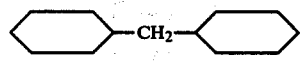

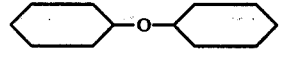

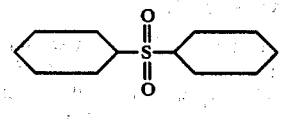

(III) Alkylene ethers

X—A—X where A is an alkylenether rarical —A(OA)$_n$ where A is alkylene (including cycloalkylene ether radicals) having for example from 1-10 or more carbons such as 1-4, but preferably 2 in each alkylene unit. Typical examples are Cl—CH$_2$CH$_2$—O—CH$_2$CH$_2$—Cl
Cl—CH$_2$CH$_2$(OCH$_2$CH$_2$)$_{1-10}$—Cl

Cl—CH$_2$CH$_2$O—CH$_2$O—CH$_2$CH$_2$—Cl

Additional examples of A include groups of the formula (AO)$_n$ where A is

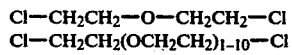

where Y is alkyl, for example

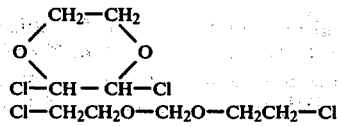

etc.

Thus, A can be methylene, polymethylene, ethylene, propylene, butylene, octylene, etc. In addition (AO)$_n$ may be homo or hetero as to A, to yield for example (ETO)$_a$ (PrO)$_b$, or (PrO—ETO)$_n$;

—CH$_2$OCH$_2$CH$_2$OCH$_2$CH$_2$OCH$_2$— etc.

These compounds also include the formal of ethylene chlorohydrin and bromohydrin, for example ClCH$_2$CH$_2$OCH$_2$OCH$_2$CH$_2$Cl, ClCH$_2$CH$_2$OCH$_2$CH$_2$OCH$_2$OCH$_2$CH$_2$OCH$_2$CH$_2$Cl etc.

(IV) Unsaturated dihalides

X—Z—X where Z is an unsaturated aliphatic radical, for example

—CH$_2$—CH=CH—CH$_2$—

—CH$_2$—C≡C—CH$_2$— etc.

The following are representative examples of the quaternaries of the present invention. Compounds I are prepared by reacting 1 mole of monofunctional quanternizing agent with 1 mole of a halogen derivative of alkynoxymethylamines and compounds II are prepared by reacting 1 mole of difunctional quaternizing agent with 2 moles of alkynoxymethylamines according to the equation:

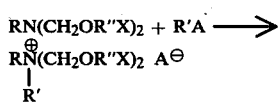

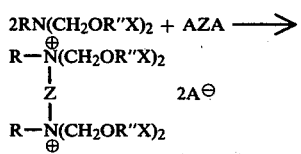

The following examples are illustrative of the present invention.

EXAMPLE 1

Into a 500 ml three-necked flask provided with a reflux condenser and stirrer were placed 18.4 g. (0.04 mole) of C$_4$H$_9$(CH$_2$OCH$_2$C≡Cl)$_2$, 5.7 g. (0.04 mole) of methyl iodide, and 20 ml. of ethanol. The reaction mixture was heated to reflux and held there for 24 hours.

The solvent was removed under reduced pressure on a rotary evaporator. The product has the following structure.

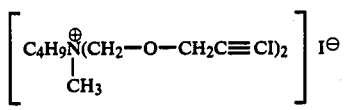

EXAMPLE 2

In a similar manner 18.4 g. (0.04 mole) of $C_4H_9N(CH_2OCH_2C\equiv CI)_2$, 5.1 g. (0.04 mole) of benzyl chloride, and 20 ml. of ethanol were refluxed together for 24 hours. The product had the following structure:

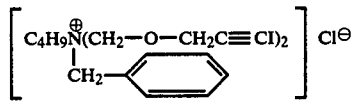

EXAMPLE 3

In a similar manner 14.8 g. (0.03 mole of

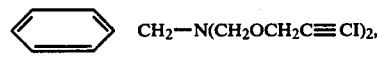

4.3 g. (0.03 mole) of methyl iodide and 20 ml, of ethanol were refluxed together for 48 hrs. The product had the following structure:

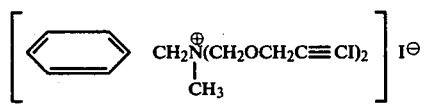

EXAMPLE 4

In a similar manner 17.9 g. (0.04 mole) of $i-C_3H_7N(CH_2OCH_2C\equiv CI)_2$, 5.7 g. (0.04 mole) of 1-bromopropane and 20 ml. of n-propanol were refluxed together for 48 hours. The product had the following structure:

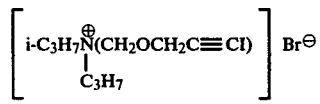

EXAMPLE 5

In a similar manner 28.7 g. (0.05 mole) of $C_{12}H_{25}N(CH_2OCH_2C\equiv CI)_2$, 7.1 g: (0.05 mole) of methyl iodide, and 40 ml. of 2-propanol were refluxed together for 60 hours. The product had the following structure:

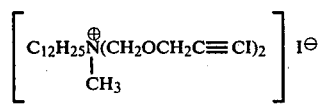

EXAMPLE 6

In a similar manner 28.7 g. (0.05 mole) of $C_{12}H_{25}N(CH_2OCH_2C\equiv CI)_2$, 6.4 g. (0.05 mole) of benzyl chloride and 40 ml. of n-propanol were refluxed together for 48 hours. The product had the following structure:

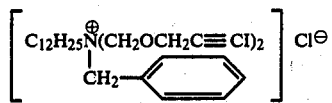

In order to avoid repetitive details the following table was constructed to further illustrate examples of this invention.

Table 1

$$\left[ R\overset{\oplus}{\underset{R'}{N}}(CH_2OR''C\equiv CX)_2 \right] A^\ominus$$

| | R | R' | R'' | X | A⁻ |
|---|---|---|---|---|---|
| Ex. 7 | $C_6H_{11}$ | $CH_3$ | $CH_2$ | I | I |
| Ex. 8 | $C_4H_9$ | $C_4H_9$ | $CH_2$ | Br | Br |
| Ex. 9 | $t-C_{12}H_{25}$ | $CH_3$ | $CH_2$ | I | I |
| Ex. 10 | $C_4H_9$ | $CH_3$ | $-\overset{H}{\underset{(CH_2)_4CH_3}{C}}-$ | I | Br |
| Ex. 11 | $C_3H_7$ | $-CH_2-\langle\rangle$ | $-\overset{CH_3}{\underset{(CH_2)_5CH_3}{C}}-$ | Br | Cl |
| Ex. 12 | $C_4H_9$ | $CH_3$ | $CH_2$ | Cl | I |

EXAMPLE 13

Into a 500 ml three-necked flask equipped with a stirrer and reflux condenser were introduced 28.7 g. (0.05 mole) of $C_{12}H_{25}N(CH_2OCH_2C\equiv CI)_2$, 5.4 g. (0.025 mole) of 1,4-dibromobutane and 35.0 ml. of n-propanol. The reaction mixture was heated at reflux for 72 hours. The isolated product had the following structure:

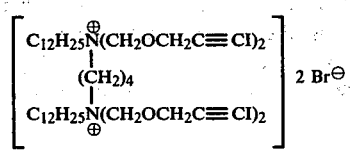

EXAMPLE 14

In a similar manner 15.0 g. (0.05 mole) of $C_4H_9N(CH_2OCH_2C\equiv CI)_2$, 5.4 g. (0.025 mole) of 1,4-dibromobutane and 15 ml. of n-propanol were refluxed together for 48 hours. The product had the following structure:

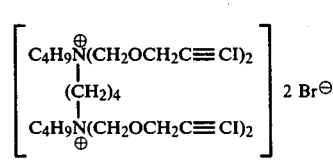

EXAMPLE 15

In a similar manner 17.9 g. (0.04 mole) of $C_3H_7N(CH_2OCH_2C\equiv CI)_2$, 2.5 g. (0.02 mole) of 1,4-dichlorobutene-2, and 10 ml. of n-propanol were refluxed together for 48 hours. The product had the following structure:

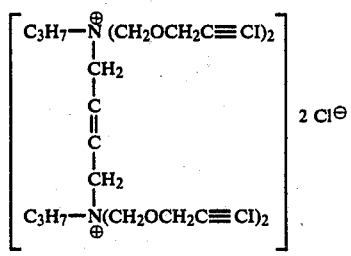

In order to avoid repetitive detail the following table was constructed to further illustrate examples of this invention:

Table 2

$$\left[ \begin{array}{c} R-\overset{\oplus}{N}(CH_2OR'C\equiv CX)_2 \\ | \\ Z \\ | \\ R-\underset{\oplus}{N}(CH_2OR'C\equiv CX)_2 \end{array} \right] \quad 2A^{\ominus}$$

| | R | R' | Z | X | A⊖ |
|---|---|---|---|---|---|
| Ex. 16 | $C_4H_9$ | $CH_2$ | $(CH_2)_6$ | Br | Br |
| Ex. 17 | $C_{12}H_{25}$ | $CH_2$ | $H_2C-\langle\bigcirc\rangle-CH_2$ | I | Cl |
| Ex. 18 | $i$-$C_3H_7$ | $CH_2$ | $(CH_2)_2O(CH_2)_2$ | I | Cl |
| Ex. 19 | $\langle\bigcirc\rangle-CH_2$ | $\begin{array}{c} H \\ | \\ -C- \\ | \\ (CH_2)_4CH_3 \end{array}$ | $(CH_2)_2$ | I | Br |
| Ex. 20 | $C_{12}H_{25}$ | $CH_2$ | $-CH_2CH=CHCH_2-$ | I | Cl |
| Ex. 21 | $C_4H_9$ | $CH_2$ | $(CH_2)_4$ | Cl | I |
| Ex. 22 | $t$-$C_{12}H_{25}$ | $CH_2$ | $(CH_2)_4$ | I | Br |

USES

This invention also relates to the inhibition of corrosion, particularly the corrosion of metals in contact with the acid solutions.

The present invention is especially useful in the acidizing or treating of earth informations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations, and which are economical to produce. The need is also for corrosion inhibitors which are effective at high temperature, e.g., 200° F. and above, such as are found in operations involving acidic solutions, particularly oil-well acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

Quaternary ammonium compounds may be illustrated by C-alkyl pyridine-N-methyl chloride quaternary, C-alkyl pyridine-N-benzyl chloride quaternary, quinoline-N-benzyl chloride quaternary, isoquinoline-N-benzyl chloride quaternary, thioalkyl pyridine quaternaries, thioquinoline quaternaries, benzoquinoline quaternaries, thiobenzoquinoline quaternaries, imidazole quaternaries, pyrimidine quaternaries, carbazole quaternaries, the corresponding ammonium compounds, pyridines and quinolines may also be used alone or in combination with the quaternary compounds. Thus a pyridine plus quinoline quaternary, a quinoline plus quinoline quaternary, or quinoline or amine alone or in combination may be used.

The formic acid compound may be selected from the esters and amides of formic acid. The formic acid compound may be from the group consisting of formate esters of the structure:

HCOOR where R is a monoaryl group, an alkyl group having 1 to 6 carbon atoms, cyclo-alkyl residues having 5 to 6 carbon atoms, alkenyl and alkynl groups having 2 to 6 carbon atoms which may contain functional groupings selected from —C—OH, —OH, =C=O, —COOH, —SH, and NH$_2$. Examples of the formic acid compound are: methyl formate, ethyl formate, benzyl formate, other alkyl and aryl formates, and the like. Other examples include formamide, dimethyl formamide, formanilide, and the like. Mixtures of the esters and mixtures of the amides may be used.

USE AS PICKLING INHIBITORS

This phase of the invention relates to pickling. More particularly, the invention is directed to a pickling composition and to a method of pickling ferrous metal. The term "ferrous metal" as used herein refers to iron, iron alloys and steel.

To prepare ferrous metal sheet, strip, etc. for subsequent processing, it is frequently desirable to remove oxide coating, formed during manufacturing, from the surface. The presence of oxide coating, referred to as "scale" is objectionable when the material is to undergo subsequent processing. Thus, for example, oxide scale must be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip or sheet. Prior to cold reduction, it is necessary that the oxide formed during hot rolling be completely removed to preclude surface irregularities and enable uniform reduction of the work.

The chemical process used to remove oxide from metal surfaces is referred to as "pickling". Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The present invention avoids the above-described problems in pickling ferrous metal articles and provides a pickling composition which minimizes corrosion, overpickling and hydrogen embrittlement. Thus the pickling inhibitors described herein not only prevent excessive dissolution of the ferrous base metal but effectively limit the amount of hydrogen absorption thereby during pickling. According to the invention, a pickling composition for ferrous metal is provided which comprises a pickling acid such as sulfuric or hydrochloric acid and a small but effective amount of the compounds of this invention, for example at least about 5 p.p.m., such as from about 100 to 50,000 p.p.m., about 500-30,000, but preferably from about 3,000 to 10,000 p.p.m.

Ferrous metal articles are pickled by contacting the surface (usually by immersion in the pickling solution) with a pickling composition as described to remove oxide from their surface with minimum dissolution and hydrogen embrittlement thereof and then washing the ferrous metal to remove the pickling composition therefrom.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

CORROSION TEST PROCEDURE

In these tests the acid solutions were mixed by diluting concentrated hydrochloric acid with water to the desired concentrations.

Corrosion coupons of N-80 steel (ASTM) were pickled in an uninhibited 10% HCl solution for 10 minutes, neutralized in a 10% solution of $NaHCO_3$, dipped in acetone to remove water and allowed to dry. They were then weighed to the nearest milligram and stored in a desicator.

In most of the tests, a 25 $cc/in^2$ acid volume to coupon surface area ratio was used. After the desired amount of acid was poured into glass bottles, the inhibitor was added. The inhibited acid solution was the placed in a water bath which had been set at a predetermined temperature and allowed to preheat for 20 minutes. After which time, the coupons were placed in the preheated inhibited acid solutions. The coupons were left in the acid solutions for the specified test time, then removed, neutralized, recleaned, rinsed, dipped in acetone, allowed to dry, then reweighed.

The loss in weight in grams was multiplied times a calculated factor to convert the loss in weight to $lbs./ft^2/24$ hrs. The factor was calculated as follows:

$$\frac{\frac{144 \text{ in}^2}{\text{ft}^2}}{\frac{454 \text{ g}}{\text{lb}} \times \text{Surface Area of Coupon (in}^2) \times \frac{1 \text{ day}}{24 \text{ hrs.}}} = \text{Factor}$$

The results of these tests are included below:

Table 3

| Inhibitor | Conc. in p.p.m. | Test Temp. °F. | Test Time Hrs. | Acid | Metal Type | Corrosion Rate (lbs/ft²/day) |
|---|---|---|---|---|---|---|
| Ex. 1 | 6000 | 200 | 4 | 15% HCl | N-80 | 0.061 |
| Ex. 2 | " | " | " | " | " | 0.052 |
| Ex. 5 | " | " | " | " | " | 0.021 |
| Ex. 6 | " | " | " | " | " | 0.014 |
| Ex. 9 | " | " | " | " | " | 0.009 |
| Ex. 13 | " | " | " | " | " | 0.051 |
| Ex. 15 | " | " | " | " | " | 0.023 |
| Ex. 22 | " | " | " | " | " | 0.011 |
| Blank | — | " | " | " | " | 1.13 |

Applications in which the inhibitors of the present invention are particularly useful include oil-well acidizing solutions, metal pickling, cleaning and polishing baths, boiler cleaning compositions and the like. They are also useful as oil soluble corrosion inhibitors, bactericides, water-in-oil demulsifying agents, surfactants and the like.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 p.p.m. to 10,000 p.p.m., or more, for example, about 50 to 5,000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 1,000 p.p.m. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

STATIC WEIGHT LOSS TESTS

The test procedure involves the measurement of the corrosive action of the fluids inhibited by the composition herein described upon sandblasted S.A.E. 1020 steel coupons measuring $\frac{5}{8}$ by $3\frac{1}{4}$ inches under conditions approximating those found in an actual producing well, and the comparison thereof with results obtained by subjecting identical test coupons to the corrosive action of identical fluids containing no inhibitor.

Clear pint bottles were charged with 200 ml. of 10% sodium chloride solution saturated with hydrogen sulfide and 200 ml. of mineral spirits and a predetermined amount of inhibitor was then added. In all cases the inhibitor concentration was based on the total volume of the fluid. Weighed coupons were then added, the bottles tightly sealed and allowed to remain at room temperature for 72 hours. The coupons were then removed, cleaned by immersion in inhibited 10% HCl, dried and weighed.

The changes in the weight of the coupons during the corrosion test were taken as a measurement of the effectiveness of the inhibitor compositions. Protection percentage was calculated for each test coupon taken from the inhibited fluids in accordance with the following formula:

$$(L_1 - L_2)/L_1 \times 100 = \% \text{ Protection}$$

in which $L_1$ is the loss in weight of the coupons taken from the uninhibited fluids and $L_2$ is the loss in weight of coupons which were subjected to the inhibited fluids.

Table 4

| | Static Weight Loss Test | |
|---|---|---|
| Ex. | Conc. of Inhibitor p.p.m. | % Protection |
| 1 | 100 | 94.3 |
| 5 | " | 98.6 |
| 6 | " | 99.2 |
| 9 | " | 99.1 |
| 13 | " | 99.8 |
| 15 | " | 93.2 |
| 22 | " | 99.7 |

Another test was conducted in order to determine the effectiveness of the corrosion inhibitors of the present invention in the corrosive medium, tap water.

Coupons of mild steel (S.A.E. 1018) having dimensions of 5 cm×3.5 cm×0.32 cm were sandblasted and cleaned. They were then weighed and placed in open beakers containing tap water to which predetermined amounts of inhibitor had been added. The beakers containing the fluid were allowed to remain at room temperature for 96 hours. The coupons were then removed, cleaned, immersed in acetone, dried, and weighed.

The changes in the weight of the coupons during the corrosion test were taken as a measurement of the effectiveness of the inhibitor compositions. Protection percentage was calculated as the ratio of the difference between the coupon weight loss with the blank and the coupon weight loss using the inhibitor, divided by the coupon weight loss of the blank, multiplied by 100.

Table 5

| | Static Weight Loss Test | |
|---|---|---|
| Composition Ex. | Conc. of Inhibitors p.p.m. | % Protection |
| 1 | 100 | 92.0 |
| 5 | 100 | 95.4 |
| 6 | 100 | 98.6 |
| 9 | 100 | 98.2 |
| 13 | 100 | 97.5 |
| 15 | 100 | 93.4 |
| 22 | 100 | 99.0 |

Note:
In each example a small amount (10 p.p.m.) of a 15 mole ethylene oxide adduct of nonyl phenol was used to help solubilize the halo derivative in the corrosive fluid.

For the above type of systems, one generally employs from about 10 to 1,000 p.p.m., such as from about 20-750 p.p.m., for example from about 30-500 p.p.m., but preferably about 50-150 p.p.m. Variations above or below this amount will depend on the particular composition employed.

The compositions of this invention are useful as microbiocides such as in water treatment, water flooding in secondary recovery of oil, treating hydrocarbons, etc. For microbiocidal use, one generally employs about 5-500 p.p.m., such as about 10-300 p.p.m., for example from about 20-200 p.p.m., but preferably about 30-100 p.p.m. Variations above or below this amount will depend on the particular composition employed.

MICROBIAL TESTING

The screening procedure was as follows: a one percent by weight solution of the test compound in water was prepared. The solution was aseptically added to a sterile broth that would support the growth of the test organism, "Desulforibrio desulfuricans," to provide a concentration of 20, 30, 40, 50 and 100 parts by weight of test compound per million parts by weight of broth. A general growth medium, such as prescribed by the American Petroleum Institute was used. The broth containing the test compound then was dispersed in 5 cc amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

Table 6

| Compound Example No. | Concentration of Test Compound |
|---|---|
| 5 | 40 |
| 6 | 30 |
| 10 | 50 |
| 13 | 30 |
| 17 | 40 |
| 20 | 40 |
| 22 | 50 |

In all of the above tests no growth of the test organism occurred, thus indicating that the compound is biostatic or a biocide.

NOTE: The compounds used were diluted to 50% by weight in isopropyl alcohol prior to testing.

I claim:

1. A process of controlling microorganisms in a water-containing system which comprises employing as a microbiocide a microbiocidal amount of a quaternary selected from quaternaries of halo alkynoxymethyl amines having one to two quaternary nitrogen atoms to each of which are attached up to two halogen derivatives of alkynoxymethyl moieties of the formula $XC\equiv CR''OCH_2-$ where $R''$ is alkylidene and X is halogen, the groups directly attached to the quaternary nitrogen atoms in the said quaternary amines being said halo alkynoxymethyl groups and being R and R' groups when there is but one quaternary nitrogen atom present per molecule and being said halo alkynoxymethyl groups and being R and Z groups when there are two quaternary nitrogen atoms present per molecule, the Z groups constituting bridging groups linking the two quaternary nitrogen atoms, the R groups being monovalent hydrocarbon, hydroxy substituted alkyl or furfuryl groups, the R' groups being monovalent hydrocarbon of up to 30 carbon atoms and the Z groups being divalent alkylene, alkenylene, alkynylene, alkaralkylene, or alkylenether groups, the counter anions balancing the positive charge on the quaternary nitrogen being halide anions.

2. The process of treating a system which comprises employing as a microbiocide a quaternary according to claim 1, wherein the quaternary has the formula

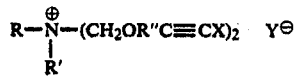

wherein R and R' are hydrocarbon groups, R" is alkylidene, X is halogen and $Y^\ominus$ is a halide anion.

3. The process of treating a system which comprises employing as a microbiocide a quaternary according to claim 1, wherein the quaternary has the formula

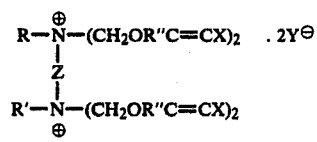

where R and R' are hydrocarbon groups, R" is alkylidene, X is halogen, $Y^\ominus$ is a halide anion, and Z is a bridging group.

4. The process according to claim 3 wherein R and R' are alkyl, aryl or aralkyl and R" is alkylidene.

5. The process according to claim 3 wherein R and R' are alkyl, aryl or aralkyl and R" is alkylidene.

6. The process according to claim 4 wherein the quaternary has the formula

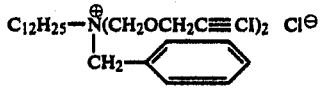

7. The process according to claim 5 wherein the quaternary has the formula

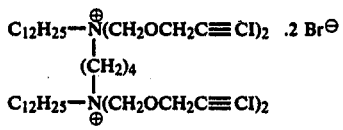

* * * * *